United States Patent [19]

Edeling et al.

[11] Patent Number: 4,612,100
[45] Date of Patent: Sep. 16, 1986

[54] METHOD FOR THE FABRICATION OF AN IMPLANTABLE ELECTRODE

[75] Inventors: Martin Edeling, Erlangen; Helmüt Freller, Röthenbach; Konrad Münd, Uttenreuth; Peter Schack, Nuremberg, all of Fed. Rep. of Germany

[73] Assignee: Siemens Aktiengesellschaft, Berlin and Munich, Fed. Rep. of Germany

[21] Appl. No.: 681,181

[22] Filed: Dec. 13, 1984

[30] Foreign Application Priority Data

Dec. 20, 1983 [DE] Fed. Rep. of Germany ....... 3345990

[51] Int. Cl.⁴ ............................................. C23C 14/34
[52] U.S. Cl. .......................... 204/192.15; 128/419 P; 128/784
[58] Field of Search ..................... 204/192 C, 192 SP; 128/419 P, 784, 785, 786

[56] References Cited

U.S. PATENT DOCUMENTS 4,011,861  3/1977  Enger ................................ 128/2.06
4,033,357  7/1977  Helland et al. .................... 128/418
4,542,752  9/1985  De Haan et al. ................... 128/784

FOREIGN PATENT DOCUMENTS 2613072  7/1981  Fed. Rep. of Germany .

OTHER PUBLICATIONS

Zivka Marinkovic and Rustum Roy, Preparation and Properties of Sputtered "Glassy" Carbon Films, Jun. 1976, pp. 329–331, vol. 14.

Primary Examiner—John F. Niebling
Assistant Examiner—William T. Leader
Attorney, Agent, or Firm—Kenyon & Kenyon

[57] ABSTRACT

In a method for manufacturing an implantable electrode, particularly a stimulating electrode, vitreous carbon is sputtered from a vitreous carbon target on at least a part of the surface of the electrode. The sputtering is performed in an argon atmosphere at a pressure of 4 to $8 \times 10^{-2}$ mbar and at a voltage of 1.6 to 2.4 kV. The electrode may consist essentially of platinum-iridium, vitreous carbon or platinum.

10 Claims, No Drawings

METHOD FOR THE FABRICATION OF AN IMPLANTABLE ELECTRODE

BACKGROUND OF THE INVENTION

This invention relates to a method for fabricating an electrode, particularly a stimulating electrode, implantable in an organism such as the human body.

Stimulating electrodes, for example, for heart pacers generally comprise an insulated cable lead and an electrode in the form of a hemisphere, a cylinder or a wire, for transmitting the stimulation pulses. Stimulation of the heart by electrical pulses, when the propagation of the stimulation is interrupted, consists of the generation of a given electric field strength at an excitable cell membrane. After the stimulation or activation is triggered, it propagates independently over the entire heart muscle and leads to its contraction.

The electrical stimulation pulses are generated by an electronic pacer which consists of an implantable electronics parts having a power supply unit and a stimulation circuit including a stimulating electrode and an indifferent electrode. During the stimulation pulse, a small capacitor is partially discharged through the stimulation circuit within 0.5 to 2 milliseconds. In the pauses between consecutive pulses the capacitor is recharged from the power supply unit, i.e., a battery. During the pulse, the field strength required for triggering the contraction of the heart muscle is present in the stimulatable tissue in the vicinity of the stimulating electrode.

Conventional stimulating electrodes, for example, of platinum, platinum-iridium or an alloy of 40 parts cobalt, 20 parts chromium, 16 parts iron, 15 parts nickel, 7 parts molybdenum and 2 parts manganese (Elgiloy) cause degeneration of the adjoining tissue because they surround themselves within a period of two to four weeks with a connective tissue layer about 0.5 to 1 mm thick which is not stimulatable. During the development of the connective tissue layer, the stimulation threshold increases steadily, i.e., an increasingly larger current is required for triggering heart contractions. The required voltage also increases. Because the distance between the stimulatable tissue and the electrode increases, more energy must be supplied to generate the same field strength at the stimulatable tissue. If the head of the stimulating electrode consists, for example, of a hemisphere with a radius of 1 mm and a connective tissue layer approximately 1 mm thick forms around the electrode, the stimulation threshold current increases fourfold. Since the voltage increases approximately to the same extent, the power required increases approximately 16 times. It is, therefore, clear that requirements as to capacity and voltage of the energy source depend to a considerable degree on the growth of the tissue at the stimulating electrode.

As described by Z. Marinkovic and R. Roy in "Preparation and Properties of Sputtered 'Glassy' Carbon Films," *Carbon*, 1976, Vol. 14, pages 329-31, vitreous carbon can be sputtered onto glass substrates, the carbon attaining a density of 0.5 to 1.79 g/cm$^3$. The deposition rate of vitreous carbon increases proportionally with the power, but the density of this sputtered-on vitreous carbon layer is inversely proportional to the power. Under the same conditions for sputtering carbon, a density of 1.58 g/cm$^3$ may be obtained for graphite as the target material, a density of 1.40 g/cm$^3$ for pyrolytic graphite, and a density of 0.74 g/cm$^3$ for vitreous carbon. The layer deposited by sputtering is not crystalline and its microstructure is grainy; it contains grains on the order of magnitude of 0.1 to 1.0 μm.

It is known to use vitreous carbon (also called "glassy carbon") as the electrode material for stimulating electrodes. An electrode head made of vitreous carbon material is superficially activated, i.e., has a surface with microporous structure in which the diameter of the pores is smaller than 0.002 μm. By activating the vitreous carbon of the electrode head, the polarization losses which occur at the boundary surface between the electrode and the tissue and which do not contribute to an increase of the field strength in the adjoining stimulatable tissue can be kept very low. An implantable electrode is thereby obtained which ensures little encapsulation by connective tissue, as well as low energy consumption and, concomitant therewith, good steady-state operation. The reason for these advantages is that the current density of the stimulation threshold does not increase for the duration of the implantation. In this known electrode the electrode head is activated in a separate operation by heating it in air to temperatures about 400° C. A slight burn-off occurs at the surface, which has a beneficial effect on the electrical properties. Macroscopically, the smooth surface of the electrode head is preserved. (See German *Auslegeschrift* No. 26 13 072.)

An object of the invention to provide a simple method of manufacturing an implantable electrode, especially a stimulating electrode, the electrode material of which is compatible with the body and has a large specific electrochemical double-layer capacity relative to the area of the electrode.

SUMMARY OF THE INVENTION

In a method for manufacturing an electrode (particularly a stimulating electrode) implantable in the tissues of a living organism, the electrode having a body portion with an outer surface, a layer of vitreous carbon is sputtered from a target of vitreous carbon onto at least a portion of the outer surface of the electrode body portion.

In accordance with another feature of the present invention, the sputtering is performed in an argon atmosphere at a pressure of 4 to $8 \times 10^{-2}$ mbar and preferably at a pressure of 5 to $7 \times 10^{-2}$ mbar and particularly $6 \times 10^{-2}$ mbar.

In accordance with yet another feature of the present invention, the step of sputtering is performed at a voltage of 1.6 to 2.4 kV, preferably 1.8 to 2.2 kV and particularly approximately 2.1 kV.

The body portion of the electrode consists essentially of platinum, platinum-iridium, vitreous carbon, or an alloy containing cobalt, chromium, iron, nickel, molybdenum, and manganese, the alloy being provided with a platinum film forming the outer surface of the electrode.

DETAILED DESCRIPTION

In accordance with the invention, vitreous carbon is sputtered onto the surface of an electrode. The electrode material may consist of platinum-iridium (Pt—Ir) and is preferably vitreous carbon or platinum. An alloy containing cobalt, chromium, iron, nickel, molybdenum and manganese (Elgiloy) can in some circumstances serve as the electrode material, a thin platinum surface film, for example, several micrometers thick being provided.

The vitreous carbon surface layer may be applied by sputtering from a vitreous carbon target in an argon atmosphere at a pressure of 4 to $8 \times 10^{-2}$ mbar, preferably about 5 to $7 \times 10^{-2}$ mbar and in particular about $6 \times 10^{-2}$ mbar, and at a voltage of 1.6 to 2.4 kV, preferably 1.8 to 2.2 kV, and in particular about 2.1 kV. The power may be 0.5 to 1.5 kW, preferably 0.8 to 1.2 kW, and in particular about 1 kW, and the deposition rate being, for example, approximately 15 nm per minute.

The vitreous carbon layer sputtered on the electrode may reach a density of approximately 0.7 g/cm$^3$. Thus, an outer electrode surface is obtained, which is not dense but microporous, i.e., a surface with pores having a diameter smaller than about 0.002 $\mu$m, the density of this surface attaining about one-half that of dense vitreous carbon and the electrode surface being nevertheless smooth macroscopically.

In contrast to the findings of practice, namely, proportionally between the argon-atmosphere pressure and the deposition rate, and the proportionality between power and density, one obtains here only a relatively small density of, for example, about 0.7 g/cm$^3$ with a relatively large power of, for example, about 1 kW.

A vitreous carbon layer applied by sputtering adheres well to an electrode and very well to a platinum electrode in particular. In addition, a platinum electrode with a porous vitreous carbon layer applied by sputtering reaches at a frequency of about 1 Hz, for example, a high electrochemical double-layer capacity of approximately 50 mF/cm$^2$. An implantable electrode thus is obtained which has very low polarization losses at the boundary surface between the electrode and the tissue, which losses do not contribute to the field strength in the adjoining stimulatable tissue. Moreover, the amount of encapsulation of the electrode by connective tissue is minimized and this ensures a low energy consumption and a good long-term operating behavior because the current density of the stimulation threshold is not increased for the duration of the implantation. These advantages, particularly the large electrochemical double-layer capacity, are obtained without additionally activating the vitreous carbon (e.g. by heating in air). Furthermore, the advantage of good contact is preserved in the case of a platinum electrode. Since platinum belongs to the metallic materials, a platinum electrode can be made and shaped in a simple manner.

In one advantageous embodiment of the implantable electrode, the electrode consists of platinum having a surface layer consisting at least partially of vitreous carbon applied via the sputtering technique. The vitreous carbon may be deposited on a predetermined portion of the electrode bead, whereby the current loading is concentrated at this sputtered-on portion. By variations in the shapes, sizes and locations of the electrode surface areas on which vitreous carbon is deposited by sputtering, a substantial improvement in energy consumption and stimulation threshold may be obtained.

In a further advantageous embodiment, platinum wires for microelectrodes or multiple electrodes for the cochlea of an artificial ear are sputtered with vitreous carbon. In this application, a large specific double-layer capacity (relative to the area) is particularly advantageous because high current densities, for example, 0.5 A/cm$^2$ are required for nerve stimulation owing to a high stimulation threshold. High polarization values can be reached by the sputtering of vitreous carbon on the surface of the electrodes.

The vitreous carbon layer sputtered on the electrode has a thickness between 1 and 20 $\mu$m, particularly a thickness of approximately 4 to 5 $\mu$m.

Although the invention has been described in terms of particular embodiments, one of ordinary skill in the art, in light of this teaching, can generate additional embodiments without departing from the spirit or exceeding the scope of the claimed invention. Accordingly, it is to be understood that the descriptions herein are proffered by way of example and should not be construed to limit the scope of the claimed invention.

What is claimed is:

1. In a method for manufacturing an electrode implantable in the tissues of a living organism, said electrode having a body portion with an outer surface, the improvement comprising the step of sputtering a layer of vitreous carbon from a target of vitreous carbon on at least a portion of the outer surface of the electrode body portion, said layer having a microporous structure and said step of sputtering being performed at a pressure 4 to $8 \times 10^{-2}$ mbar and at a voltage of 1.6 to 2.4 kV with a power input 0.5 to 1.5 kW.

2. The improvement defined in claim 1 wherein said step of sputtering is performed in an argon atmosphere at a pressure of 5 to $7 \times 10^{-2}$ mbar.

3. The improvement defined in claim 2 wherein said step of sputtering is performed in an argon atmosphere at a pressure of approximately $6 \times 10^{-2}$ mbar.

4. The improvement defined in claim 1 wherein said step of sputtering is performed at a voltage of 1.8 to 2.2 kV.

5. The improvement defined in claim 4 wherein said step of sputtering is performed at a voltage of approximately 2.1 kV.

6. The improvement defined in claim 1 wherein said body portion consists essentially of platinum.

7. The improvement defined in claim 1 wherein said body portion consists essentially of platinum-iridium.

8. The improvement defined in claim 1 wherein said body portion consists essentially of vitreous carbon.

9. The improvement defined in claim 1 wherein said body portion consists essentially of an alloy containing cobalt, chromium, iron, nickel, molybdenum, and manganese and is provided with a platinum film forming said outer surface.

10. The improvement defined in claim 1 wherein the step of sputtering is performed in an argon atmosphere.

* * * * *